United States Patent
Taylor et al.

(10) Patent No.: US 7,189,236 B2
(45) Date of Patent: Mar. 13, 2007

(54) VERTEBRAL ARTHRODESIS EQUIPMENT

(76) Inventors: Jean Taylor, 25, Avenue Poralto, Cannes (FR) F-06400; Bernard Villaret, 20, Rue de Salles, Croix Chapeau (FR) F-17220; Patrizio Parisini, Via Pastrengo No 8, Bolonge (IT) I-40123; Jean-Luc Clement, 230, Chemin Monfort, La Colle sur Loup (FR) F-06480

( * ) Notice: Subject to any disclaimer, the term of this patent is extended or adjusted under 35 U.S.C. 154(b) by 433 days.

(21) Appl. No.: 10/415,900

(22) PCT Filed: Nov. 5, 2001

(86) PCT No.: PCT/FR01/03412

§ 371 (c)(1),
(2), (4) Date: Oct. 15, 2003

(87) PCT Pub. No.: WO02/38061

PCT Pub. Date: May 16, 2002

(65) Prior Publication Data

US 2004/0092931 A1  May 13, 2004

(30) Foreign Application Priority Data

Nov. 7, 2000  (FR) .................................. 00 14270

(51) Int. Cl.
*A61B 17/56* (2006.01)
(52) U.S. Cl. ........................................................ 606/61
(58) Field of Classification Search .................. 606/61, 606/72, 59
See application file for complete search history.

(56) References Cited

U.S. PATENT DOCUMENTS

| | | | | |
|---|---|---|---|---|
| 5,352,224 A | * | 10/1994 | Westermann | 606/61 |
| 5,584,831 A | * | 12/1996 | McKay | 606/61 |
| 6,267,765 B1 | * | 7/2001 | Taylor et al. | 606/61 |
| 6,273,914 B1 | * | 8/2001 | Papas | 623/17.11 |
| 6,306,136 B1 | * | 10/2001 | Baccelli | 606/61 |

FOREIGN PATENT DOCUMENTS

| | | |
|---|---|---|
| EP | 0 383 992 | 8/1990 |
| WO | WO 00 59387 | 10/2000 |

* cited by examiner

*Primary Examiner*—Eduardo C. Robert
*Assistant Examiner*—Michael J. Araj
(74) *Attorney, Agent, or Firm*—Young & Thompson

(57) ABSTRACT

The invention concerns an equipment comprising two shoring rods, members for anchoring said two rods to the vertebrae, at least a crosspiece (1) in two parts (5, 6) and members (2) assembling said crosspiece (1) to the shoring rods. The invention is characterised in that one of the crosspiece parts (5) comprises a spherical head (7) and a thread (8) adjacent to said head (7); the other crosspiece part (6) comprises a spherical bulging end (9), defining internally a spherical cavity (10) adapted to receive said head (7), and each crosspiece (1) comprises a nut (12) designed to cooperate with said thread (8), including further a spherical seat (13) with a shape matching that of the wall (11) delimiting the cavity (10). The invention also concerns plates (30for anchoring the equipment to the sacrum.

20 Claims, 3 Drawing Sheets

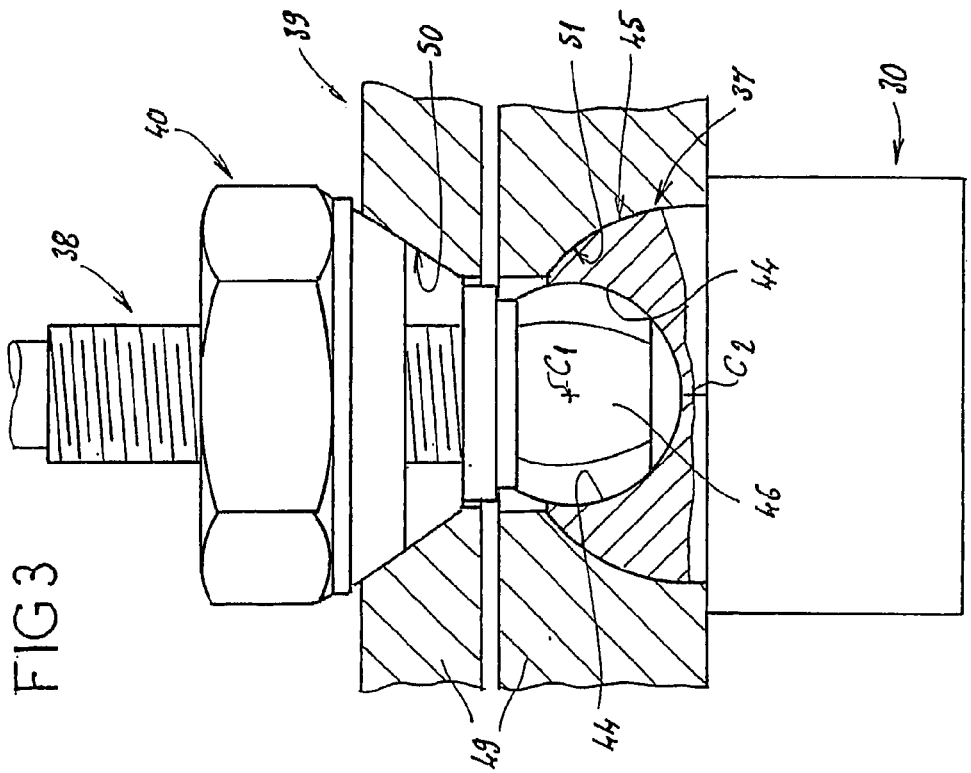
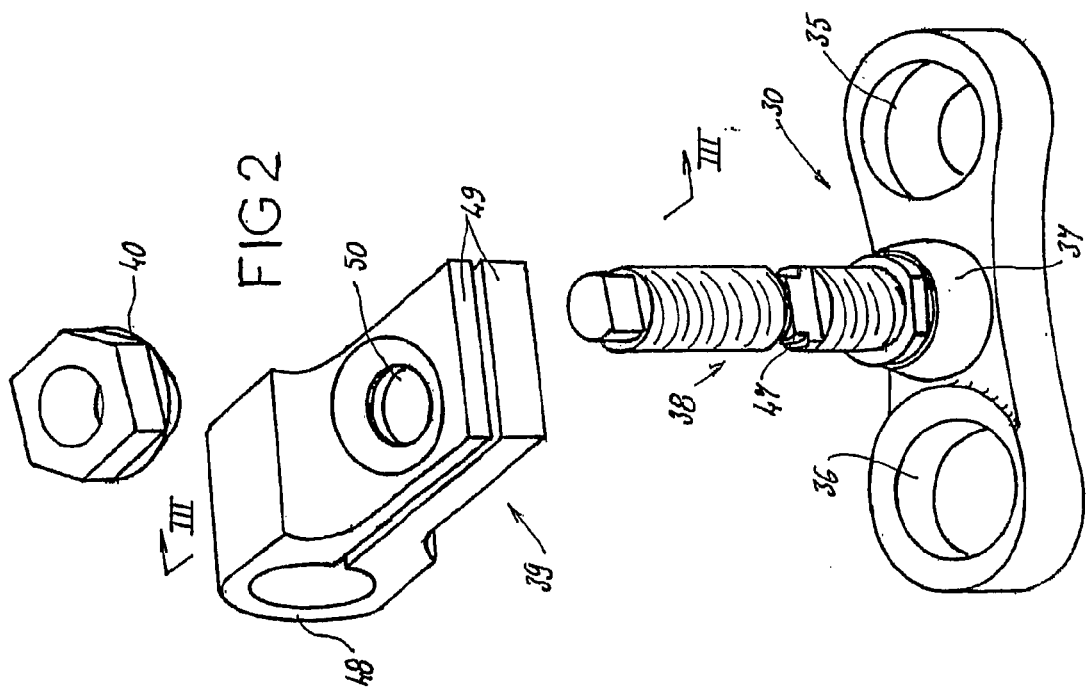

VERTEBRAL ARTHRODESIS EQUIPMENT

FIELD OF THE INVENTION

The present invention relates to a vertebral arthrodesis equipment.

DESCRIPTION OF THE RELATED ART

Usually such equipment includes two parallel shoring rods attached to either side of the vertebrae and anchoring members of these rods to the vertebrae, such as hooks or pedicule screws. These equipment may also include cross-pieces running between the two rods in order to keep them in place.

These cross-pieces in some cases consist of simple one-piece members, linked to the support rods with an appropriate attachment member. The one-piece members are inconvenient in that they cannot adapt to all situations, in particular not being able to accommodate all the different possible positions of the shoring rods. Especially, the separation between the support rods may vary from one place to another, or the support rods may be oriented in different planes.

Two-part cross-pieces have been developed that can pivot in one plane in relation to each other. However these cross-pieces only partially remedy the above mentioned problems.

Furthermore, the attachment members for the shoring rods of existing equipment do not perform satisfactorily. These members are either relatively complex and difficult to manufacture, or are awkward and raise the cross-pieces above the shoring rods to such a degree that they become noticeable under the skin, or leave doubts as to the long term durability of the assembly.

The invention aims mainly to eliminate these problems.

Furthermore, the attachment of existing equipments to the sacrum is relatively problematic, due to the lack of an anchoring member well adapted to fixing the shoring rods to the sacrum.

The invention also aims to offer a solution to this problem.

The equipment concerned includes two shoring rods placed parallel to each other on either side of the vertebrae to be treated, anchoring members to attach these rods to the vertebrae, such as hooks or pedicule screws, at least one two-part cross-piece, and attachment members to attach this cross-piece to the shoring rods.

BRIEF SUMMARY OF THE INVENTION

According to the invention:

one of the cross-piece parts comprises a spherical head at its extremity intended to be connected to the other part of the cross-piece, and a thread adjacent to this head;

the other cross-piece part has a spherical bulging end, defining internally a spherical cavity adapted to receive said head, with the possibility of movement of the head within the cavity, the inner surface of the cavity fitting around the head in such a way as to retain the head within the cavity, and each cross-piece comprises a nut design to co-operate with said thread, including further a spherical seat matching that of the wall delimiting the cavity.

The head and spherical cavity thus form a ball and socket joint enabling multidirectional movement of one part of the cross-piece in relation to the other. The cross-piece according to the invention is thus able to accommodate all likely situations, in particular orientations of the shoring rods in different planes. When the appropriate relative position of the two parts of the cross-piece is determined, the nut is tightened on the thread until it comes against the wall of the bulging end and exerts some pressure thereon. This pressure creates a tension on the head relative to the bulging end and friction between them which enable the two parts of the cross-piece to be fixed to each other.

Advantageously, the equipment includes a screw to connect one of the cross-piece part to the member that enables the attachment of this part of the cross-piece to the corresponding shoring rod, and this part of the cross-piece includes an oblong opening allowing a choice of positions for this screw, and thus for the attachment member, relative to that part of the cross-piece.

The cross-piece may thus be adapted to different separations of the shoring rods.

Preferably, each of the cross-piece parts have an oblong opening as described, to enable the maximum possible adaptation of the cross-piece to different separations of the shoring rods.

Preferably, each cross-piece part comprising said oblong opening has several recesses which, either individually or in pairs, form circular seatings designed to receive the head of the aforementioned screw.

These seatings thus define several positions for the screw relative to the corresponding part of the cross-piece, and prevent the screw from moving within the oblong opening after being tightened.

In a preferred embodiment of the invention, each attachment member includes a one-piece member that has:

a recess crossing the member and forming two lateral clamping walls, for receiving a shoring rods and tightening this shoring rods;

an L-shaped slot running in the same direction as the aforementioned recess; one part of the L-shaped slop opens laterally into the recess, and is roughly parallel to the clamping walls; the other part of the slot is in a roughly perpendicular direction to the clamping walls and is relatively long, so that each clamping wall is connected to the rest of the member by a relatively narrow section thereby offering elasticity, and two coaxial bores, the first of which does not have a thread and passes through a first part of the member, defined by the face of the member opposite to the recess and by said other part of the L-shaped slot, and the second, with a thread, which runs through a second part of the member, defined by the second part of the aforementioned L-shaped slot and by the recess.

A screw may thus pass through an opening in a cross-piece part and then through the first bore and be screwed into the second threaded bore. Tightening of this screw then causes said first part of the member to come closer to said second part of the member, by a slight distortion of the member. This distortion enables the tightening of the aforementioned clamping walls around a shoring rods placed in the seating.

The attachment member thus created is simple to manufacture, robust, and enables secure fixing of the shoring rods.

Another part of the invention involves two fixing plates to attach the shoring rods to the sacrum, each having attachment means to the corresponding shoring rods;

each plate has two lateral holes able to receive fixing screws, one of the holes having an axis roughly perpendicular to the face by which the plate is to be mounted onto the sacrum, and the other hole having an axis at an angle of about 60 degrees relative to this same face;

the attachment means of each plate comprises:
(i) a domed part of the plate, internally forming, with the plate, a spherical cavity and externally forming a spherical surface; the centres generating the hollow sphere which forms said cavity and said spherical surface being offset one relative to the other in a direction perpendicular to the plate;
(ii) a threaded rod with a spherical head that fits into and can be held in the above mentioned cavity, this head being designed to co-operate with the cavity in such a way to allow movement of the rod relative to the plate;
(iii) a stirrup with a rounded part able to receive a shoring rod, and two flanges with superimposed holes to enable this stirrup to be attached to the aforementioned threaded rod; and a surface having a form of hollow sphere portion, this surface being designed to bear against said spherical surface when the stirrup is mounted on the threaded rod, and
(iv) a nut that may be tightened on the threaded rod so as to enable the tightening of the stirrup between the nut and the spherical surface.

When the equipment is being put into place the threaded rod may, due to the cavity and the spherical head, be aligned with the direction of the stirrup, itself attached beforehand around the shoring rod. This alignment facilitates the engagement of the stirrup's eyelets with the threaded rod.

The nut may then be mounted on the threaded rod and screwed on, having the effect of bringing the concave face of the stirrup into contact with the spherical face of the above mentioned domed part and then, once this contact has been made, and taking into account the above mentioned offset of the said centres, of gradually bringing, as the nut is tightened, the threaded rod into a direction approximately perpendicular to the plate.

This attachment member thus facilitates the positioning of the equipment, and enables a gradual alignment of the shoring rods relative to the fixing plates.

For purposes of clarification, the invention is described below again, reference being made to the attached drawings, which offer a non restrictive example of a preferred embodiment of the equipment.

BRIEF DESCRIPTION OF THE DRAWINGS

FIG. 2 is an exploded view of a fixing plate for attaching the equipment to the sacrum.

FIG. 3 is a cross section of this plate through the line III—III of FIG. 2.

DETAILED DESCRIPTION OF THE INVENTION

Figure 1:
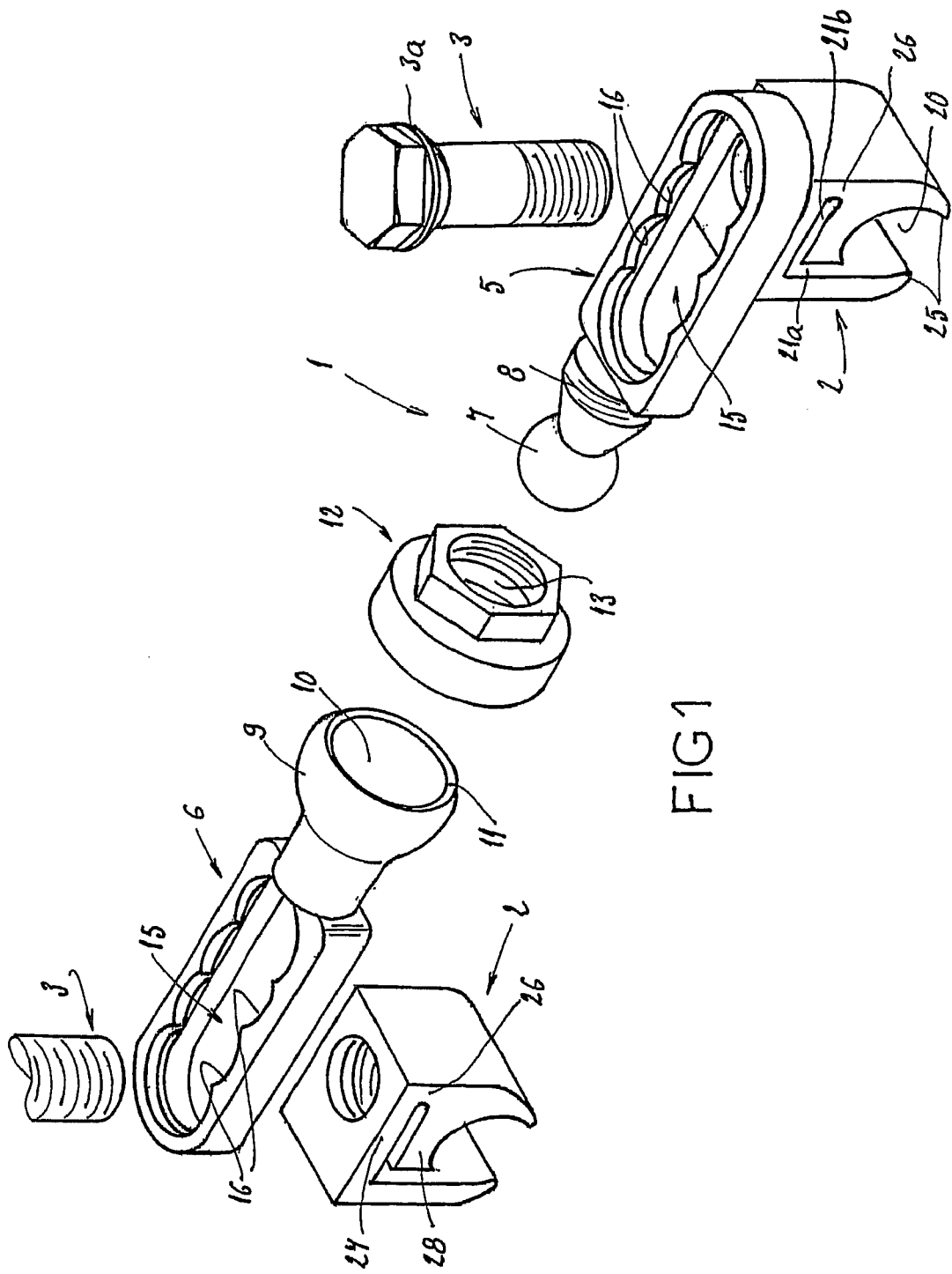
FIG. 1 is an exploded view of a cross-piece, two attachment pieces, and two screws that the equipment comprises.

FIG. 1 shows a cross-piece 1, the attachment pieces 2, and the screws 3, that are part of the vertebral arthrodesis equipment.

This equipment also includes two shoring rods to be placed parallel to each other on either side of the vertebrae to be treated, and anchoring members for attaching these rods to the vertebrae, such as hooks or pedicle screws. These rods and anchoring members are well-known and are therefore not fully described.

As FIG. 1 shows, the cross-piece 1 is in two parts 5 and 6. Part 5 has a spherical head 7 at its extremity that is intended to be connected to part 6, and a thread 8 adjacent to the head 7. Part 6 has a spherical bulging end 10 that receives the head 7 with the possibility of movement of this head 7 within the cavity 10. The inner surface of the cavity 10 fits around the head 7 in such a way as to retain the head within the cavity 10.

The cross-piece 1 also includes a nut 12 mounted on the part 5, that is able to co-operate with the thread 8. The nut 12 has a spherical flange 13 having a shape that corresponds to the shape of the cavity 11.

Each part of the cross-piece 5, 6 has an oblong opening 15, through which passes a screw 3, and which has a number of individual or pairs of circular recesses 16 into which the head 3a of the screw 3 may fit.

Each attachment piece 2 is a one-piece member and has a seating 20, an L-shaped slot 21a and 21b, and two coaxial bores.

The seating 20 is made up as from one of the edges of part 2, and runs through the part 2. It is circular and has a diameter very slightly larger than that of the shoring rods, so that the shoring rods will fit snugly into the seating 20. It has thus two lateral clamping walls 25.

The L-shaped slot runs through part 2 in the same direction as the seating 20. One portion 21a of this slot opens laterally into the seating 20, in a direction parallel to the walls 25. The other portion of the slot 21b runs perpendicular to the walls 25 and has an important length. In this way, each wall 25 is joined to the rest of the part 2 by a relatively narrow section 26, having a certain elasticity. The slot thus defines two zones 27 and 28 of part 2, zone 27 being defined by the surface of part 2 opposite the seating 20 and by the portion 21b of the slot 21, and zone 28 being defined by the portion 21b of the slot 21 and by the seating 20.

Concerning the two coaxial bores, one runs through zone 27 and does not have a thread, the other runs through zone 28 and does have a thread.

The screw 3 has a head 3a allowing it to sit in parts 5 and 6 at the circular recesses 16, and a shaft that can be passed through the openings 15 and then through the non threaded bore in part 2, finally engaging in the threaded bore in part 2.

The head 7 and the cavity 10 form a ball and socket joint enabling multidirectional movement of one part 5 of the cross-piece relative to the other 6, in such a way that the cross-piece can accommodate any likely situation, especially concerning the separation and direction of the shoring rods. The nut 12 enables a tension to be created on the head 7 relative to the extremity 9 and the friction between them enables parts 5 and 6 of the crosspiece to be fixed relative to each other.

Tightening of each screw 3 causes zone 28 and zone 27 to move closer to each other as a result of the distortion of part 2. This distortion causes the walls 25 to tighten around a shoring rod placed within the seating 20.

Figure 4:
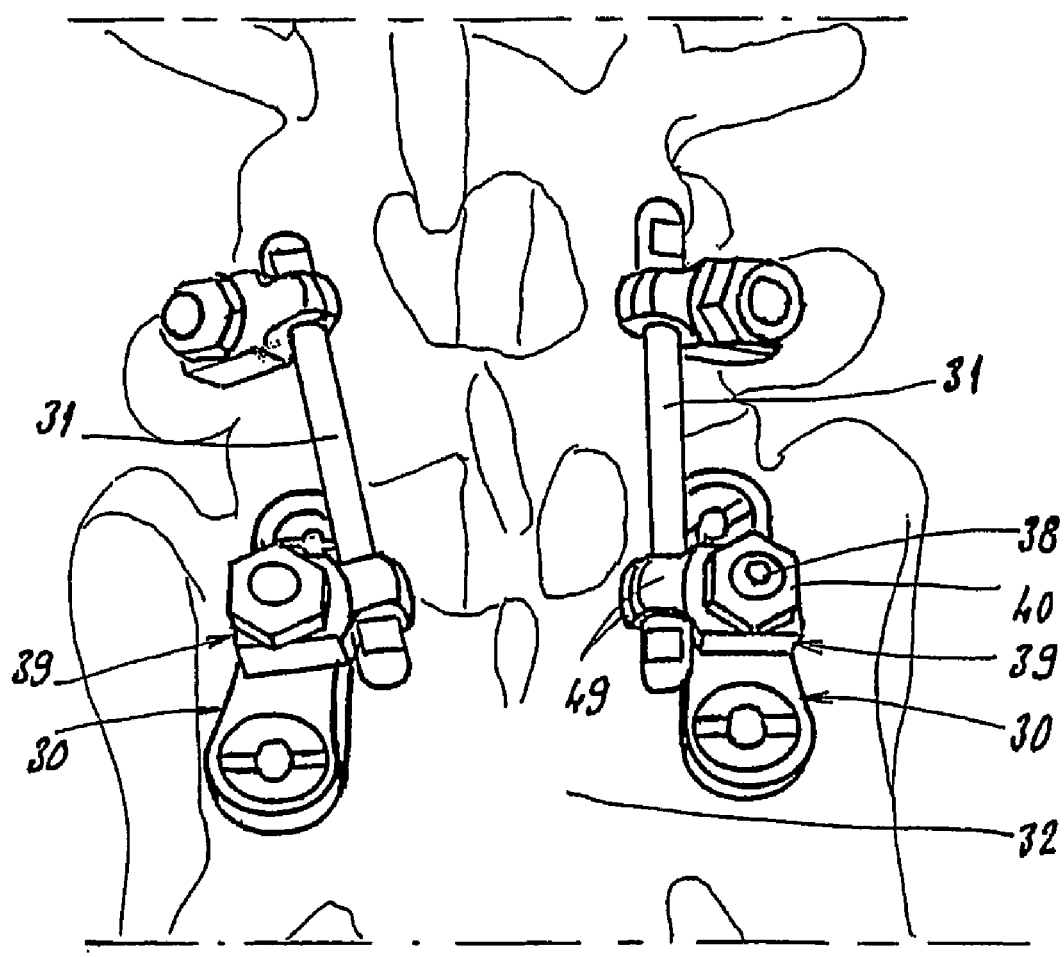
FIG. 4 shows the plates and the rest of the equipment after attachment to the sacrum.

As shown in FIG. 4, the arthrodesis equipment also includes two fixing plates 30 to secure the shoring rods 31 to the sacrum 32.

FIGS. 2 and 3 show the lateral holes 35 and 36 through these fixing plates 30 designed to receive fixing screws, and a raised central part 37 on which is mounted a shaft with a thread 38. A stirrup 39 may be attached to this shaft with a nut 40.

Each hole 35 has an axis roughly perpendicular to the face that goes against the sacrum 32 whilst each hole 36 has an axis at an angle of approximately 60 degrees relative to this same face.

The raised part 37 is connected to the plate 30. Internally, there is a spherical cavity 44 on the plate 30, externally there is a spherical surface 45.

As shown in FIG. 3, the centre of the sphere C1 that forms the cavity 44 and the centre of the of the sphere C2 that forms the spherical surface 45 are offset in a direction perpendicular to the surface of the plate 30.

The threaded shaft 38 has a spherical head 46 that fits into the cavity 44. This head 46 is designed to engage with the cavity in such a way as to enable movement of the shaft 38 relative to the plate 30.

The shaft 38 also has a thinner section 47 enabling the shaft to be cut once the equipment has been put in place.

The stirrup 39 consists of a rounded section that holds a shoring rod, and two superimposed flanges 49 with holes 50 in them to allow the stirrup 39 to be mounted on the shaft 38, and a concave spherical surface 51. This concave spherical surface, as can be seen in FIG. 3, fits onto the spherical surface 45 when the stirrup 39 is mounted on the shaft 38.

The nut 40 engages with the shaft 38 so as to allow a tightening of the stirrup 39 onto the spherical surface 45.

Because of the cavity 44 and the spherical head 46, the shaft 38 may, during the fitting of the equipment, be positioned in the direction of the stirrup 39, which has already been attached to a shoring rod. This positioning facilitates the alignment of the holes 50 in the stirrup 39 with the shaft 38.

The nut 40 may thus be mounted on the shaft 38 and tightened, with the result that the above mentioned surface 51 of the stirrup is brought into contact with the above mentioned spherical surface 45. Once this takes place, given the offset of the centres C1 and C2 aforementioned, the shaft 38 may gradually be brought into an alignment roughly perpendicular to the plate 30 as the screw 40 is tightened.

The invention thus provides a vertebral arthrodesis equipment with considerable advantages over previous similar equipment.

The invention is not of course limited to the form described in the example given here, but may also be applied in all the forms covered by the attached claims.

The invention claimed is:

1. A vertebral arthrodesis equipment, comprising:
two shoring rods adapted to be placed parallel to each other on either side of vertebrae to be treated;
anchoring members to attach said rods to the vertebrae;
at least one two-part cross-piece; and
attachment members to attach said two-part cross-piece to said shoring rods, each attachment member comprises a one-piece member, wherein, each one-piece member comprises:
a recess crossing said one-piece member and forming two lateral clamping walls for receiving and tightening around a shoring rod;
an L-shaped slot running in the same direction as said recess, such that said L-shaped slot has a part roughly parallel to said clamping walls that opens laterally into said recess and a part roughly perpendicular to said clamping walls;
said perpendicular part of said L-shaped slot being sufficiently long, so that each clamping wall is connected to said one-piece member by a section sufficiently narrow to provide elasticity; and
two coaxial bores, wherein a first non-threaded bore passes through a first part of said one-piece member, defined by a surface of said one-piece member opposite said recess and by said L-shaped slot part perpendicular to the clamping walls, and a second threaded bore passes through a second part of said one-piece member, defined by the L-shaped slot part perpendicular to the clamping walls and by the recess.

2. The equipment according to claim 1, wherein each attachment member further comprises a screw, each screw has a shaft with thread corresponding to the second threaded bore of said one-piece member and a head, and each cross-piece part includes an oblong opening sized to receive said screw shaft and allowing a choice of positions for each screw, and thus for the attachment member, relative to said cross-piece.

3. The equipment according to claim 2, wherein said oblong opening enables different separations of the shoring rods.

4. The equipment according to claim 3, wherein each cross-piece part comprising said oblong opening has several recesses which form circular seatings designed to receive screw head.

5. The equipment according to claim 3, wherein:
one of said cross-piece parts has a spherical head at an extremity and a thread adjacent to said spherical head;
the other cross-piece part has a spherical bulging end defining an internal spherical cavity proportioned to receive said spherical head and allow movement of said spherical head within said spherical bulging end cavity, said spherical bulging end cavity fitting around said spherical head in such a way as to retain said spherical head within said spherical bulging end cavity; and
a nut having a thread to cooperate with said screw thread of one cross-piece part and a spherical seat to match that of the wall delimiting said spherical bulging end cavity of the other cross-piece part.

6. The equipment according to claim 3, wherein each of said anchoring members comprises:
two fixing plates to attach said shoring rods to a sacrum including the vertebrae, wherein,
each plate comprises:
a face that is to be mounted against the sacrum, two lateral holes able to receive fixing screws, one of the holes having an axis roughly perpendicular to said face by which the plate is to be mounted onto the sacrum, and the other hole having an axis at an angle of about 60 degrees relative to said face;
a domed part internally forming a spherical cavity and externally forming a spherical surface, the centers of said domed part spherical cavity and said domed part spherical surface being offset one relative to the other in a direction perpendicular to said plate;
a threaded rod with a spherical head proportioned to fit into and be held by said domed part spherical cavity, said spherical head being designed to co-operate with said domed part spherical cavity in such a way to allow movement of said rod relative to said plate;
a stirrup with a rounded part able to receive a shoring rod, two flanges with superimposed holes to enable this stirrup to be attached said threaded rod, and a surface having a form of hollow sphere portion being designed to bear against said domed part spherical surface when said stirrup is mounted on said threaded rod; and
a nut that may be tightened on said threaded rod so as to enable the tightening of the stirrup between said nut and said domed part spherical surface of said plate.

7. The equipment according to claim 2, wherein said oblong opening has a plurality of recesses which form circular screw head seatings.

8. The equipment according to claim 7, wherein,
one of said cross-piece parts has a spherical head at an extremity and a thread adjacent to said spherical head;
the other cross-piece part has a spherical bulging end defining an internal spherical cavity proportioned to receive said spherical head and allow movement of said spherical head within said spherical bulging end cavity, said spherical bulging end cavity fitting around said spherical head in such a way as to retain said spherical head within said spherical bulging end cavity; and
a nut having a thread to co-operate with said screw thread of one cross-piece part and a spherical seat to match that of the wall delimiting said spherical bulging end cavity of the other cross-piece part.

9. The equipment according to claim 4, wherein each of said anchoring members comprises:
two fixing plates to attach said shoring rods to a sacrum including the vertebrae, wherein,
each plate comprises:
a face that is to be mounted against the sacrum, two lateral holes able to receive fixing screws, one of the holes having an axis roughly perpendicular to said face by which the plate is to be mounted onto the sacrum, and the other hole having an axis at an angle of about 60 degrees relative to said face;
a domed part internally forming a spherical cavity and externally forming a spherical surface, the centers of said domed part spherical cavity and said domed part spherical surface being offset one relative to the other in a direction perpendicular to said plate;
a threaded rod with a spherical head proportioned to fit into and be held by said domed part spherical cavity, said spherical head being designed to co-operate with said domed part spherical cavity in such a way to allow movement of said rod relative to said plate;
a stirrup with a rounded part able to receive a shoring rod, two flanges with superimposed holes to enable this stirrup to be attached said threaded rod, and a surface having a form of hollow sphere portion being designed to bear against said domed part spherical surface when said stirrup is mounted on said threaded rod; and
a nut that may be tightened on said threaded rod so as to enable the tightening of the stirrup between said nut and said domed part spherical surface of said plate.

10. The equipment according to claim 2, wherein,
one of said cross-piece parts has a spherical head at an extremity and a thread adjacent to said spherical head;
the other cross-piece part has a spherical bulging end defining an internal spherical cavity proportioned to receive said spherical head and allow movement of said spherical head within said spherical bulging end cavity, said spherical bulging end cavity fitting around said spherical head in such a way as to retain said spherical head within said spherical bulging end cavity; and
a nut having a thread to co-operate with said screw thread of one cross-piece part and a spherical seat to match that of the wall delimiting said spherical bulging end cavity of the other cross-piece part.

11. The equipment according to claim 2, wherein each of said anchoring members comprises:
two fixing plates to attach said shoring rods to a sacrum including the vertebrae, wherein,
each plate comprises:
a face that is to be mounted against the sacrum,
two lateral holes able to receive fixing screws, one of the holes having an axis roughly perpendicular to said face by which the plate is to be mounted onto the sacrum, and the other hole having an axis at an angle of about 60 degrees relative to said face;
a domed part internally forming a spherical cavity and externally forming a spherical surface, the centers of said domed part spherical cavity and said domed part spherical surface being offset one relative to the other in a direction perpendicular to said plate;
a threaded rod with a spherical head proportioned to fit into and be held by said domed part spherical cavity, said spherical head being designed to co-operate with said domed part spherical cavity in such a way to allow movement of said rod relative to said plate;
a stirrup with a rounded part able to receive a shoring rod, two flanges with superimposed holes to enable this stirrup to be attached said threaded rod, and a surface having a form of hollow sphere portion being designed to bear against said domed part spherical surface when said stirrup is mounted on said threaded rod; and
a nut that may be tightened on said threaded rod so as to enable the tightening of the stirrup between said nut and said domed part spherical surface of said plate.

12. The equipment according to claim 1, wherein,
one of said cross-piece parts has a spherical head at an extremity and a thread adjacent to said spherical head;
the other cross-piece part has a spherical bulging end defining an internal spherical cavity proportioned to receive said spherical head and allow movement of said spherical head within said spherical bulging end cavity, said spherical bulging end cavity fitting around said spherical head in such a way as to retain said spherical head within said spherical bulging end cavity; and
a nut having a thread to co-operate with said screw thread of one cross-piece part and a spherical seat to match that of the wall delimiting said spherical bulging end cavity of the other cross-piece part.

13. The equipment according to claim 12, wherein each of said anchoring members comprises:
two fixing plates to attach said shoring rods to a sacrum including the vertebrae, wherein,
each plate comprises:
a face that is to be mounted against the sacrum, two lateral holes able to receive fixing screws, one of the holes having an axis roughly perpendicular to said face by which the plate is to be mounted onto the sacrum, and the other hole having an axis at an angle of about 60 degrees relative to said face;
a domed part internally forming a spherical cavity and externally forming a spherical surface, the centers of said domed part spherical cavity and said domed part spherical surface being offset one relative to the other in a direction perpendicular to said plate;
a threaded rod with a spherical head proportioned to fit into and be held by said domed part spherical cavity, said spherical head being designed to co-operate with said domed part spherical cavity in such a way to allow movement of said rod relative to said plate;
a stirrup with a rounded part able to receive a shoring rod, two flanges with superimposed holes to enable this stirrup to be attached said threaded rod, and a surface having a form of hollow sphere portion being designed to bear against said domed part spherical surface when said stirrup is mounted on said threaded rod; and a nut that may be tightened on said threaded rod so as to enable the tightening of the stirrup between said nut and said domed part spherical surface of said plate.

14. The equipment according to claim 1, wherein each of said anchoring member comprises:
- two fixing plates to attach said shoring rods to a sacrum including the vertebrae, wherein,
- each plate comprises:
- a face that is to be mounted against the sacrum, two lateral holes able to receive fixing screws, one of the holes having an axis roughly perpendicular to said face by which the plate is to be mounted onto the sacrum, and the other hole having an axis at an angle of about 60 degrees relative to said face;
- a domed part internally forming a spherical cavity and externally forming a spherical surface, the centers of said domed part spherical cavity and said domed part spherical surface being offset one relative to the other in a direction perpendicular to said plate;
- a threaded rod with a spherical head proportioned to fit into and be held by said domed part spherical cavity, said spherical head being designed to co-operate with said domed part spherical cavity in such a way to allow movement of said rod relative to said plate;
- a stirrup with a rounded part able to receive a shoring rod, two flanges with superimposed holes to enable this stirrup to be attached said threaded rod, and a surface having a form of hollow sphere portion being designed to bear against said domed part spherical surface when said stirrup is mounted on said threaded rod; and
- a nut that may be tightened on said threaded rod so as to enable the tightening of the stirrup between said nut and said domed part spherical surface of said plate.

15. The equipment according to claim 14 wherein said threaded rod includes a shaft that has a thinner section enabling said threaded rod to be cut once the equipment has been fitted.

16. A vertebral arthrodesis equipment comprising:
- two shoring rods;
- a vertebrae anchoring member;
- a two-part cross-piece; and
- shoring rod attachment members, wherein said shoring rod attachment members comprise one-piece members, and each of said one-piece members comprises:
- two lateral clamping walls extending from a surface forming a receiving recess for tightening around a shoring rod;
- an L-shaped slot, part of said L-shaped slot being roughly parallel to said clamping walls and a part of said L-shaped slot roughly perpendicular to said clamping walls, said roughly perpendicular part extending sufficient length so that each clamping wall is connected to said surface by a section sufficiently narrow to provide elasticity to said clamping walls, and said L-shaped slot creating a first zone between said surface and said roughly perpendicular part and second zone between said roughly perpendicular part and said recess;
- two coaxial bores, wherein a first non-threaded bore runs through the first zone and a second threaded bore runs through the second zone.

17. The equipment of claim 16, wherein said shoring rod attachment members further comprise screws, wherein each of said screws comprises a shaft having thread corresponding to the second threaded bore of said one-piece member and a head.

18. The equipment of claim 16, wherein each part of said two-part cross-piece comprises am oblong opening sized to receive a screw and allow a choice of positions for a screw.

19. The equipment of claim 16, wherein said two part cross-piece comprises:
- a first cross-piece part having a spherical head at an extremity and a thread adjacent to said spherical head;
- a second cross-piece part having a spherical bulging end defining an internal spherical cavity, wherein said spherical head and spherical cavity are proportioned to form a ball and socket joint enabling multidirectional movement of each part cross-piece part relative to the other; and
- a nut having a thread to co-operate with said first part thread and a spherical seat to match that of the wall delimiting said spherical bulging end of said second part.

20. The equipment of claim 16, wherein said vertebrae anchoring member comprises a fixing plate for attaching said shoring rod to a sacrum, said fixing plate comprises:
- a sacrum mounting face with two lateral fixing screw holes;
- a domed part having an external spherical surface and internal spherical cavity;
- a threaded rod with a spherical head proportioned to fit into and be held by said internal spherical cavity, said rod being moveable relative to said plate when held by said internal spherical cavity;
- a stirrup with a rounded shoring rod receiving part, two flanges with superimposed holes proportioned to attach to said threaded rod, and a surface having a hollow sphere portion proportioned to bear against said external spherical surface of said domed part when said stirrup is mounted on said threaded rod; and
- a nut sized for said threaded rod to enable the tightening of the stirrup between said nut and said external spherical surface of said domed part of said plate.

\* \* \* \* \*